United States Patent
Myers et al.

(10) Patent No.: US 11,383,988 B2
(45) Date of Patent: Jul. 12, 2022

(54) OOLITIC ARAGONITE BEADS AND METHODS THEREFOR

(71) Applicant: Calcean Minerals and Materials, LLC, Gadsden, AL (US)

(72) Inventors: Anthony Myers, Gadsden, AL (US); Alyson Myers, Gadsden, AL (US); Harold Meherg, Culver City, CA (US); Patrick Soon-Shiong, Culver City, CA (US)

(73) Assignees: Nant Holdings IP, LLP, Culver City, CA (US); Calcean Minerals and Materials, LLC, Gadsden, AL (US)

( * ) Notice: Subject to any disclaimer, the term of this patent is extended or adjusted under 35 U.S.C. 154(b) by 0 days.

(21) Appl. No.: 16/858,548

(22) Filed: Apr. 24, 2020

(65) Prior Publication Data

US 2020/0308015 A1    Oct. 1, 2020

Related U.S. Application Data

(60) Provisional application No. 62/964,500, filed on Jan. 22, 2020, provisional application No. 62/951,899, (Continued)

(51) Int. Cl.
*C01F 11/18* (2006.01)
*C09C 1/02* (2006.01)
(Continued)

(52) U.S. Cl.
CPC ............ *C01F 11/185* (2013.01); *A61K 8/042* (2013.01); *A61K 8/19* (2013.01); *A61K 8/733* (2013.01);
(Continued)

(58) Field of Classification Search
None
See application file for complete search history.

(56) References Cited

U.S. PATENT DOCUMENTS

| 4,910,224 A * | 3/1990 | Habib ............... A61K 31/23 |
| | | 514/558 |
| 6,753,002 B2 | 6/2004 | George et al. |

(Continued)

FOREIGN PATENT DOCUMENTS

CN    102814222 A    12/2012

OTHER PUBLICATIONS

"Aquarium." (c) 2018 CaribSea.com, viewed on Sep. 8, 2020 at https://caribsea.com/aquarium/.*
(Continued)

*Primary Examiner* — Daniel Berns
(74) *Attorney, Agent, or Firm* — Martin Fessenmaier; Umberg Zipser LLP

(57) ABSTRACT

Disclosed herein are personal care and/or cosmetic compositions, comprising a carrier and oolitic aragonite beads having an average diameter between 10 nm to 10 mm. Also disclosed herein are methods of reducing plastic contamination and/or pollution comprising making a cosmetic or personal care composition, wherein at least a portion to all (100%) of the plastic microbeads in the cosmetic or personal care composition are replaced with oolitic aragonite. Also disclosed herein are a milling system and milling methods for producing oolitic aragonite particles having a clean top size in which the particles are screened to remove any oversized particles. Additional uses include drug-loaded aragonite particles for therapeutic drug delivery and chromatography media.

10 Claims, 2 Drawing Sheets

In order of largest presence of the Mineral or Compound

| # | Description | Chemical Symbol | ASTM Test | SGS | Thornton | Units | Expected Range | |
|---|---|---|---|---|---|---|---|---|
| | | | | | | | Low | High |
| 1 | Calcium Carbonate | $CaCO_3$ | ASTM C-25 | 95.57% | 93.49% | Percentage Dry | 92% | 98% |
| 2 | Strontium Carbonate | $SrCO_3$ | ASTM C-1271 | no test | 1.50% | Percentage Dry | 1% | 2% |
| 3 | Magnesium Carbonate | $MgCO3$ | ASTM C-1271/25 | 0.44% | 0.83% | Percentage Dry | 0.40% | 1.00% |
| 4 | Sulfur Trioxide | $SO_3$ | ASTM C-25 | 0.07% | 0.36% | Percentage Dry | 0.05% | 0.50% |
| 5 | Sodium Chloride | NaCl | ASTM C-471 | 650 | 531 | Part Per Million | 400 | 800 |
| 7 | Silicon Monoxide/Dioxide | $SiO / SiO_2$ | ASTM C-1271/25 | 200 | 300 | Part Per Million | 0 | 400 |
| 6 | Aluminum/Boron | $Al_2O_3$/B | ASTM C-25/6010 | Less than 200 | Less than 220 | Part Per Million | 0 | 200 |
| 8 | Iron Oxide | $Fe_2O_3$ | ASTM C-1271/25 | 110 | 150 | Part Per Million | 0 | 200 |
| 9 | Zinc | Zn | ASTM C-25/6010 | no test | 24 | Part Per Million | 0 | 100 |
| 10 | Copper/Lead | Cu/Pb | ASTM C-25/6010 | Less than 20 | Less than 20 | Part Per Million | 0 | 50 |

Related U.S. Application Data filed on Dec. 20, 2019, provisional application No. 62/902,314, filed on Sep. 18, 2019, provisional application No. 62/839,322, filed on Apr. 26, 2019.

(51) Int. Cl.

| | | |
|---|---|---|
| *A61K 8/19* | (2006.01) | |
| *A61K 8/64* | (2006.01) | |
| *A61K 8/04* | (2006.01) | |
| *A61K 8/73* | (2006.01) | |
| *B01J 20/04* | (2006.01) | |
| *A61K 8/44* | (2006.01) | |

(52) U.S. Cl.
CPC ............... *C09C 1/024* (2013.01); *A61K 8/44* (2013.01); *A61K 8/64* (2013.01); *A61K 2800/10* (2013.01); *A61K 2800/412* (2013.01); *A61K 2800/621* (2013.01); *C01P 2004/51* (2013.01); *C01P 2004/61* (2013.01)

(56) References Cited

U.S. PATENT DOCUMENTS

| | | | |
|---|---|---|---|
| 2002/0012681 A1 | 1/2002 | George et al. | |
| 2004/0139920 A1 | 7/2004 | Carty et al. | |
| 2004/0161388 A1 | 8/2004 | Liu et al. | |
| 2017/0056318 A1 | 3/2017 | Dieye et al. | |
| 2017/0142978 A1* | 5/2017 | Falken | A01N 65/03 |
| 2017/0369329 A1* | 12/2017 | Paynter | D21H 17/67 |

OTHER PUBLICATIONS

Bodge, "Beach Nourishment with Aragonite and Tuned Structures." Coastal Engineering Practice, 1992, pp. 73-89; viewed on Sep. 8, 2020 at https://www.olsen-associates.com/sites/default/files/docs/pubs/Bodge_Beach%20nourishment%20with%20aragonite%201992.pdf.*

US Aragonite Enterprises, "Oshenite(R) Products." Captured by Internet Archive Wayback Machine on Feb. 10, 2018 (viewed on Dec. 10, 2020, URL in file).*

US Aragonite Enterprises, "Oshenite(R) Plastics Enhancers Product Catalog 2014." (2014) (viewed on Dec. 11, 2020) at http://aragonite.us/docs/catalog_OsheniteProducts_06.pdf.*

Omari et al., "Profiles of Drug Substances, Excipients, and Related Methodology", Calcium Carbonate, 2016, vol. 41, pp. 31-132 (Cited from Specification).

Yong et al., "Alginate: Properties and biomedical applications", Progress in Polymer Science, 2012, vol. 37, No. 1, pp. 106-126 (Cited from Specification).

Kamba et al., "Synthesis and Characterisation of Calcium Carbonate Aragonite Nanocrystals from Cockle Shell Powder (*Anadara granosa*)", Journal of Nanomaterials, 2013, vol. 2013, No. 398357, pp. 1-9 (Cited from Specification).

Kamba et al., "A pH-Sensitive, Biobased Calcium Carbonate Aragonite Nanocrystal as a Novel Anticancer Delivery System", BioMed Research International, 2013, vol. 2013, No. 587451, pp. 1-10 (Cited from Specification).

Omari et al., "Calcium Carbonate", Chapter 2, 2016, 102 pages (Cited from Specification).

International Search Report and Written Opinion received fro PCT Application Serial No. PCT/US2020/029949 dated Aug. 7, 2020, 14 pages.

International Preliminary Report on Patentability Chapter 1 received for PCT Application Serial No. PCT/US2020/029949 dated Nov. 4, 2021, 12 pages.

\* cited by examiner

| In order of largest presence of the Mineral or Compound | | | | | | Expected Range | |
|---|---|---|---|---|---|---|---|
| # | Description | Chemical Symbol | ASTM Test | SGS | Thornton | Units | Low | High |
| 1 | Calcium Carbonate | CaCO3 | ASTM C-25 | 95.57% | 93.49% | Percentage Dry | 92% | 98% |
| 2 | Strontium Carbonate | SrCO3 | ASTM C-1271 | no test | 1.50% | Percentage Dry | 1% | 2% |
| 3 | Magnesium Carbonate | MgCO3 | ASTM C-1271/25 | 0.44% | 0.83% | Percentage Dry | 0.40% | 1.00% |
| 4 | Sulfur Trioxide | SO3 | ASTM C-25 | 0.07% | 0.36% | Percentage Dry | 0.05% | 0.50% |
| 5 | Sodium Chloride | NaCl | ASTM C-471 | 650 | 531 | Part Per Million | 400 | 800 |
| 6 | Silicon Monoxide/Dioxide | SiO / SiO2 | ASTM C-1271/25 | 200 | 300 | Part Per Million | 0 | 400 |
| 7 | Aluminum/Boron | Al2O3/B | ASTM C-25/6010 | Less than 200 | Less than 220 | Part Per Million | 0 | 200 |
| 8 | Iron Oxide | Fe2O3 | ASTM C-1271/25 | 110 | 150 | Part Per Million | 0 | 200 |
| 9 | Zinc | Zn | ASTM C-25/6010 | no test | 24 | Part Per Million | 0 | 100 |
| 10 | Copper/Lead | Cu/Pb | ASTM C-25/6010 | Less than 20 | Less than 20 | Part Per Million | 0 | 50 |

Aragonite (1) → Grizzly Feed Hopper (2) → Electro Magnetic (3) → Fluid Bed Dryer (4) → Screen (5) → Ball Mill (6) → Air Classifier (7) → Heat Jacketed Mixer (8) → To Packaging Rejects (from Air Classifier back to Ball Mill)

1. Aragonite delivered from source in the Bahamas
Typical Sieve Analysis

| Mesh Size | % Retained | % Cumulative |
|---|---|---|
| >1" | 0.20% | 0.20% |
| >/= 4 Mesh | 0.20% | 0.40% |
| >/= 24 mesh | 7.50% | 7.90% |
| </+ 80 Mesh | 88.50% | 96.40% |
| < 80 Mesh | 3.60% | 100% |

Feed contains 2-3% Amino Acids

2. Grizzly Feed Hopper with 2" grizzly bars

3. Electro Magnet to prevent metal contamination

4. Fluid Bed Dryer - Outlet Temp - 260F
   Moisture - <0.20%
   Rate - 6,500 - 7000 lbs/hr 5. Screen Stacked
   1"
   4 Mesh
   10 Mesh
   24 Mesh
   80 Mesh 6. Ball Mill
   a. Grate Discharge
   b. 4' X 12' dimensions.
   c. Ceramic Lined
   d. Metal Grinding Media 3/8" 45% Volume
   e. Grinding Aid rate 12-15 cc/min
   f. Grinding aid used - HEA-2/MTDA 632
   g. 125 - 175 hp/ton @ 2-3um 7. Air Classification
   a. MS-10 Model
   b. OEM - Micro Sizer
   c. Fines Recovery ~ 12-20%

8. Heated Mixer
   a. Hot Oil Jacketed
   b. Product Temp 280 +/- 10 F
   c. Palm based steric acid used at 1.6-1.9%
   d. Must account for Amino Acid on organic LOI

OOLITIC ARAGONITE BEADS AND METHODS THEREFOR

This application claims priority to and the benefit of U.S. Provisional Application No. 62/839,322 filed on Apr. 26, 2019; U.S. Provisional Application No. 62/902,314 filed on Sep. 18, 2019; U.S. Provisional Application No. 62/951,899 filed on Dec. 20, 2019; and U.S. Provisional Application No. 62/964,500 filed on Jan. 22, 2020, the entire contents of all of which are incorporated herein by reference.

FIELD OF THE INVENTION

The field of the invention is personal care and cosmetic compositions having oolitic aragonite beads, and pearl compositions made from the oolitic aragonite beads and milling methods and systems for making the oolitic aragonite beads.

BACKGROUND

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

US 2002/0012681 to George et al. reports cosmetic compositions comprising fluorescent minerals. Aragonite is reported as a mineral with strong brightness.

Small plastic beads with a diameter of typically less than 1 mm (<1 mm)—also known as microbeads—are currently used in many ways, for example, as cleansing or exfoliating agents in cosmetics, soaps, or toothpaste. Microbeads used in personal care products typically migrate through drains, and ultimately pollute oceans and lakes. A United Nations study found that a typical exfoliating shower gel contains as much microplastic by weight as the packaging in which the gel is packaged. A single tube of toothpaste can contain 300,000 microplastic spheres. Problematically, plastic microbeads do not dissolve or degrade, such that they continue to pollute the environment long after they have been used.

According to a recent report, there over $10^6$ microplastic particles per $km^2$ in Lake Erie, and up to 25,000 microplastic particles per $km^2$ in Lake Huron. See also, NPR Morning Edition, "Why Those Tiny Microbeads In Soap May Pose Problem For Great Lakes," May 21, 2014. "They are about the same size as fish eggs, which means that, essentially, they look like food. To any organism that lives in the water, they are food." See id. Thus, the concern is that these plastic microbeads are making their way into the food web.

Moreover, microbeads bind and concentrate various environmental toxins. When ingested by fish and crustaceans these toxins enter the food chain at high quantities, which further enrich upwards toward humans at the top of the food chain. Additionally, microplastics per se harm a dynamic ecosystem. The primary concern for human health, however, is more urgently the toxins and carcinogens used to make these microplastics.

Furthermore, calcium carbonate is one of the most abundant materials found in the earth's crust and it forms rock types of limestone and chalk. Calcium carbonate is also the most abundant chemical sediment in modern and most ancient oceans, making up roughly 10% of the ocean sediments. (M. M. H. Al Omari et al., Chapter Two, Calcium Carbonate, page 34, *Profiles of Drug Substances, Excipients, and Related Methodology*, Vol. 41, 2016 Elsevier Inc. ISSN 1871-5125.)

Currently, calcium carbonate utilized in the marketplace is processed as or from ground calcium carbonate (GCC), precipitated calcium carbonate (PCC) (synthesized), and/or limestone production. The product produced is a commodity grade with different attributes. To get a clean particle sized distribution (PSD) top size and low retain, most companies utilize a wet grinding process by either high solids or low solids. However, the product and these processes are neither biogenic nor environmentally favorable.

Thus, there remains a need for new personal care and cosmetic compositions that replace the plastic beads with alternative products, while still providing the scrubbing properties of plastic microbeads. Moreover, such alternative products should be biodegradable, and safe to humans and the environment.

SUMMARY

The present disclosure sets forth systems and methods for producing ground aragonite particles having low variation in the particle size distribution (PSD). In particular, the ground aragonite particles are made following a rigorous yet cost effective and environmentally favorable method rendering a clean top size in which the particles are screened to remove any oversized particles.

Compositions made following the disclosed methods and/or using the disclosed system include ground aragonite particles having a size of between 2.0 to 3.5 microns in which 0.005% of the particles are retained on 325 mesh.

More specifically, the inventive subject matter includes a method for producing ground aragonite particles including drying aragonite particles having an average size of 750 um to 1 mm, milling the dried aragonite particles in a ball mill, wherein the ball mill includes metal grinding media, a grinding aid, and a grate discharge. The method includes separating the ground aragonite particles in an air classifier that separates the ground aragonite particles having a selected particle size distribution, wherein the temperature of the aragonite particles processed is maintained below 200° C.

In specific embodiments, the method includes milling using a ball mill at 70 to 80% of the optimum speed, wherein the optimum speed is the speed at which centrifugal force at the top of the mill equals the force of gravity. Preferably the grinding aid used in the ball mill is HEA-2/MTDA 632.

In additional embodiments, the method for producing ground aragonite particles also includes surface treating the ground aragonite particles having the selected particle size distribution. For example, for rendering aragonite particles having a hydrophobic surface, the surface treatment is preferably steric acid.

Notably, the inventive subject matter also includes a closed circuit system for producing the ground aragonite particles. The closed circuit system includes a feed hopper, a fluid bed dryer, a ball mill, and an air classifier fluidly coupled to each other for form a continuous path for a feed of aragonite moving from the feed hopper through to the air classifier. More specifically, the feed hopper is a grizzly feed hopper including grizzly bars. The ball mill includes metal grinding media, a grate discharge, and a ceramic lining. The air classifier separates ground aragonite particles of the selected size for output and directs oversized aragonite particles to the ball mill.

In additional embodiments, the closed circuit system as disclosed above and herein, also includes an electromagnet that is fluidly coupled between the feed hopper and the fluid bed dryer. Additionally, the closed circuit system may also include a screen stack fluidly coupled between the fluid bed dryer and the ball mill.

For applying a surface treatment, the closed circuit system as disclosed above and herein, may also include a heat jacked mixer fluidly coupled to the air classifier capable of receiving the ground aragonite particles of the selected size.

The aragonite particles described herein can be used in drug delivery. In some embodiments, the composition of aragonite particles made by the contemplated methods are loaded with a molecule (e.g., a drug molecule). The aragonite particle may be surface treated prior to loading with the molecule. Examples of molecules include small molecules such a chemotherapeutics as well as large molecules including proteins such as antibodies. The surface treated aragonite particles may be further functionalized to bind a small molecule or protein.

Additionally, the aragonite particles described herein may be used as an adsorbent chromatography media. The aragonite particles may be hydrophilic or hydrophobic. Accordingly, the aragonite particles may be surface treated as disclosed herein to produce the desired charge. The aragonite particles may also be further functionalized with a binding moiety to produce chromatography media capable of binding and isolating more specific targets.

The present disclosure also sets forth various compositions of, methods for, and use of oolitic aragonite in personal care and cosmetic compositions for various uses. Therefore, personal care and/or cosmetic compositions are disclosed herein, comprising a carrier and oolitic aragonite beads having an average particle size between 100 nm to 1 mm. In some embodiments, the carrier may be a water-soluble alginate hydrogel, resulting in a composition that is mostly or completely ocean-derived. The alginate hydrogel and the oolitic aragonite may form a dispersion solution. The pH of the composition is generally more than 7.0, as oolitic aragonite has a slightly alkaline pH of 8.2 to 8.4. The personal care composition may be formulated as exfoliating scrubs, bath lotions, soap bars, shampoos, conditioners, toothpastes, or lotions. Alternatively, the cosmetic composition may also be formulated as foundation, lipstick, mascara, face serums, eyeshadow, highlighter, or contour cosmetics.

In some embodiments, the oolitic aragonite is coupled to a protein, which may provide an added beneficial effect. The composition may further comprise one or more cosmetically acceptable surfactants, such as an anionic surfactant, a nonionic surfactant, an amphoteric surfactant, a zwitterionic surfactant, and combinations thereof. The carrier in the composition may comprise a cosmetically acceptable ingredient selected from the group consisting of a solvent, an emulsifier, a surfactant, a structuring agent, a thickener or gelling agent, a skin conditioning agent, a filler, a fiber, a sunscreen agent, a preservative, a chelator, an antioxidant, a neutralizing or pH-adjusting agent, a cosmetically active agent or dermatologically active agent, a flavonoid, a colorant, an aesthetic agent, a foam enhancer, a botanical extract, an anti-inflammatory agent, a protein (e.g., a serum protein or an enzyme), and mixtures thereof.

The instant disclosure also provides a non-therapeutic, cosmetic method for cleansing and/or brightening the skin and/or producing visual skin homogeneity, comprising topically applying the composition disclosed above.

The average size of the oolitic aragonite for use in the presently disclosed compositions and methods depends on the particular use, and generally it is between 100 nm and 1 mm in diameter. Alternatively or additionally, at least half of the oolitic aragonite particles have a size between 100 nm and 1 mm in diameter.

Also disclosed herein is a method of reducing plastic contamination and/or pollution comprising: making a cosmetic or personal care composition, wherein at least a portion of the plastic microbeads that might otherwise have been used in the cosmetic or personal care composition are replaced with oolitic aragonite. In one embodiment, the oolitic aragonite has a size distribution sufficient to give an exfoliating character. Preferably, the oolitic aragonite has an average particle size between 100 μm and 3 mm in diameter, or at least 50% of the oolitic aragonite have a particle size between 100 μm and 3 mm in diameter. In another embodiment, the oolitic aragonite particles have a size distribution sufficient to give an iridescence in a cosmetic composition. Preferably, to provide an iridescence, the oolitic aragonite has an average particle size between 10 nm to 1 μm in diameter, and/or at least 50% of the oolitic aragonite has an average particle size between 10 nm to 1 μm in diameter. In another embodiment, the oolitic aragonite has a size distribution sufficient to be a filler in a cosmetic. When used as a filler, the oolitic aragonite has an average particle size between 10 μm and 100 μm in diameter, and/or at least 50% of the oolitic aragonite has an average particle size between 10 μm and 100 μm in diameter.

In some embodiments, the pH of the personal care product is more than 7.0. In some embodiments, oolitic aragonite beads are coupled to protein. Preferably, the personal care product is toothpaste, an exfoliating product, a soap bar, or a shampoo. When the personal care product is a toothpaste, it may further comprise a sweetener, such as sorbitol or saccharin to provide a pleasant taste. When the personal care product is a cleanser, it may further comprise a surfactant, such as an anionic surfactant, nonionic surfactant, amphoteric surfactant, zwitterionic surfactant, and combinations thereof. In some embodiments, the composition further comprises a cosmetically acceptable ingredient selected from the group consisting of solvents, emulsifiers, surfactants, structuring agents, thickeners or gelling agents, skin conditioning agents, fillers, fibers, sunscreen agents, preservatives, chelators, antioxidants, neutralizing or pH-adjusting agents, cosmetically active agents or dermatologically active agents, flavonoids, colorants, aesthetic agents, foam enhancers, botanical extracts, anti-inflammatory agents, vitamins, and mixtures thereof.

Also disclosed herein is a cosmetic composition having a soft focus effect with radiance, comprising: a light reflecting medium comprising oolitic aragonite having average particle size of about 1 nm to 100 um; and a cosmetically acceptable carrier system. In one embodiment, the oolitic aragonite amounts to 0.1% (w/w) to 30% (w/w) of the composition. In one embodiment, the composition may be aqueous based, comprising from about 30% (w/w) to about 90% (w/w) water of the composition. The oolitic aragonite may be platelet shaped, spherical shaped, or oval shaped. In one embodiment, the oolitic aragonite may be coated with another substance. Preferably, the oolitic aragonite particles are coated with titanium dioxide and/or mica.

The instant disclosure also discloses a method for making a synthetic pearl composition where the method includes providing the presently disclosed aragonite microbeads to a pressure device and applying pressure to the aragonite microbeads in the pressure device. Applied pressure may be of between 4,000 to 10,000 pounds per square inch (psi). The applied pressure may be from one or multiple directions. For example, the applied pressure may be a balanced pressure. The pressure device may a roller device having at least two rollers in between which the aragonite microbeads are provided. Additionally, or alternatively, the pressure device includes a mold for containing the aragonite microbeads wherein the mold is capable of receiving the applied pressure. A synthetic pearl composition may be obtained following the presently disclosed methods.

Various objects, features, aspects and advantages of the subject matter disclosed herein will become more apparent from the following figures and detailed description of preferred embodiments.

BRIEF DESCRIPTION OF THE DRAWING

FIG. 1 is a table of exemplary results for chemical analysis of aragonite.

FIG. 2 is an exemplary schematic of a closed circuit ball mill system.

DETAILED DESCRIPTION

As known to a skilled artisan, plastic microbeads are widely used in cosmetics as exfoliating (or structuring or massaging) agents and as mild abrasive or polishing agent in personal care products such as toothpaste. Oolitic aragonite can be used in a variety of manners to replace plastic beads in personal care products. Oolitic aragonite can also be used to impart a specific visual character, and especially iridescent appearance. Moreover, oolitic aragonite will not act as an irritant to skin, oral mucosa, etc., even upon prolonged exposure. Still further, due to generally hydrophilic character, oolitic aragonite will not adsorb or otherwise bind various hydrophobic environmental toxins. In contrast, oolitic aragonite could even be associated with various desirable hydrophilic agents due to the porosity of the oolitic aragonite.

As used herein, "microbeads" are manufactured particles of ≥5 mm in their largest dimension (see C. Copeland: Microbeads: An Emerging Water Quality Issue, fas.org, Jul. 20, 2015). As used herein, "plastic" conveys polyethylene, polypropylene, polyethylene terephthalate, polymethyl methacrylate, polytetrafluoroethylene, and nylon polymer materials. Plastic microbeads are commercially available in particle sizes from 10 micrometers to 5 millimeter. However, such plastic microbeads cause pollution in the water, and ultimately may enter the food chain. Advantageously, oolitic aragonite may be used in place of plastic beads. In most cases, oolitic aragonite beads are naturally biodegradable. The biodegradable oolitic aragonite microbeads disclosed herein are stable in typical formulations commonly used in cosmetics and personal care products, but will degrade in time when exposed to an ambient environment outside the formulation.

The oolitic aragonite of the present disclosure can be obtained from any biogenic aragonite source including mollusk shells and calcareous endoskeleton of warm- and cold-water corals, or as inorganic precipitates as marine cements. Where oolitic aragonite is obtained from organic sources, organic molecules (e.g., proteins, lipids, etc.) in the aragonite (calcium carbonate minerals) can be removed by any suitable procedures (e.g., protease treatment, etc.) before using in the instant compositions.

Oolitic aragonite is one of the purest forms of naturally precipitated calcium carbonate. It has a crystalline morphology of orthorhombic, bipyramidal, characteristically needle-shaped crystals. Oolitic aragonite can be processed to recrystallize and/or reform in various shapes, such that it can be used for various purposes that take advantage of the mechanical and chemical properties of the calcium carbonate minerals. The table in FIG. 1 provides exemplary results for chemical analysis of aragonite. Oolitic aragonite particles as disclosed herein are solid matter having a regular (e.g., spherical, or ovoid) or irregular shape. Thus, in one preferred embodiment herein, the oolitic aragonite may have a spherical, cubic, cone, cuboid, or prism shape when it is used as an exfoliator in a personal care composition, while the oolitic aragonite may have a platelet shape when it is used in a cosmetic composition for radiance.

Natural aragonite, for example oolitic aragonite, may be prepared to a desired shape and size, depending on the particular use of the aragonite. In one embodiment, the aragonite is dried and screened to a variety of gradations. In one embodiment, the aragonite particles are cut to approximate desired particle sizes by crushing the aragonite with a steel mortar and a pestle, and/or milling (e.g., jet milling, attrition milling, ball milling, etc.). Additionally or alternatively, the crushed or milled particles can be shaped into a spherical or platelet shape by passing the reduced particles through a platelet- or sphere-making machine normally used in the stone and rock industry.

Oolitic aragonite's adsorption capacity is a function of three parameters: (1) surface charge (also known as "$\zeta$ (zeta) potential"); (2) surface area/void ratio; and (3) particle solubility. By accurately measuring these three parameters, one can determine what materials will adsorb to aragonite particle surfaces under given conditions.

A positive charge on a particle surface will bind anions, while a negative surface charge binds cations. Aragonite $\zeta$ potential is a function of pH. Specifically, aragonite typically adsorbs cations at pH>8, but adsorb anions at pH<8. The $\zeta$ potential of aragonite affects the stability of colloidal dispersions containing aragonite. The $\zeta$ potential indicates the degree of repulsion among adjacent, similarly charged particles in a dispersion. Dispersions with high potentials will resist aggregation. When $\zeta$ potential is low, flocculates form because attraction exceeds repulsion. Oolitic aragonite has a $\zeta$ potential greater than 25 mV in most circumstances, and therefore oolitic aragonite dispersions typically resist coagulation or flocculation. As a result, aragonite can resist breaking and flocculation when combined with many other chemicals.

Berlin and Khabakov (1961) report that biogenic $CaCO_3$ typically has a negative $\zeta$ potential, while mineral-origin $CaCO_3$ typically has a very low to positive $\zeta$ potential. Particle solubility and $\zeta$ potential control what adsorbs to the aragonite surface, while surface area/void ratio control the adsorptive capacity. Particles with larger surface areas can adsorb more material to their surface. For example, aragonite needs a positive $\zeta$ potential to bind nitrate ($NO_3^-$). Therefore, where aragonite is to be included in a filter to remove nitrate, the filtered media's pH should be kept low to achieve the necessary $\zeta$ potential.

Oolitic aragonite also has a naturally high number of measurable pores in particles with diameters less than 2 nm (i.e., a high "microporosity"). Highly microporous materials are useful in applications such as catalysis, separation, absorption, and as delivery vehicles for chemicals.

The diameter of the aragonite microbeads depends on the final use of the particles. For example, if the oolitic aragonite is to be used for exfoliation purpose, the particle size is between 1 µm and 10 mm, or more preferably between 500 µm and 5 mm, and most preferably between 100 µm and 3 mm in diameter. Alternatively, at least 30%, at least 50%, at least 70%, or at least 90% of the oolitic aragonite particles have an average size between 1 µm and 10 mm in diameter, or more preferably between 10 µm and 5 mm in diameter, and most preferably between 100 µm and 3 mm in diameter. On the other hand, if the oolitic aragonite is used in a cosmetic makeup application, for example to provide iridescence to the skin, or to provide a soft focus effect with radiance, the particle size of the oolitic aragonite would be smaller, for example between 1 nm to 100 µm, or more preferably between 10 nm to 1 µm, and most preferably between 100 nm to 500 nm. Aragonite microbeads in these smaller ranges (e.g., from 1 nm to 100 µm) may be referred to as aragonite powder. Alternatively, at least 30%, at least 50%, at least 70%, or at least 90% of the oolitic aragonite particles have an average size between 1 nm to 100 µm in diameter, or more preferably between 10 nm to 1 µm in diameter, and most preferably between 100 nm to 500 nm in diameter. Thus, as disclosed throughout this disclosure, the size and shape of the oolitic aragonite depends on its final use.

Indeed, it should be appreciated that the aragonite may be physically and/or chemically modified to so enhance or mitigate certain features of the aragonite. For example, in some embodiments the aragonite will be dried to reduce the moisture content at least some degree. Among other drying parameters, it is contemplated that the aragonite is dried to a moisture content of equal or less than 5.0%, or equal or less than 2.5%, or equal or less than 1.0%, or equal or less than 0.8%, or equal or less than 0.6%, or equal or less than 0.4%, or equal or less than 0.2% moisture content. Moreover, it should be recognized that the aragonite materials may be subject to specific selection/separation of particle sizes to accommodate to particular purposes. For example, the aragonite may be milled or otherwise comminuted to obtain a desired size range. In one embodiment, comminution will be performed using a ceramic lined ball mill and steel balls to grind the oolitic aragonite into a fine product of various micron sizes (e.g., 2-8 micron, 12-18 micron, 20-40 micron), which is deemed to be especially suitable for cosmetics and other personal care products.

As will be readily appreciated, the comminuted material can be separated to different gradations for specific purposes. For example, where the comminuted aragonite is used for microbeads for facial and body scrubs, the aragonite can be dried and screened aragonite using specific mesh ranges.

For example, a mesh with 80 openings per square inch of screen is denoted as an 80 mesh screen. A "+" before the mesh size indicates the particles are retained by the sieve. A "−" before the mesh size indicates the particles pass through the screen). The coarsest material sent contains all particles that can pass a 30 mesh screen and be retained on a 40 mesh screen. The particle size range for this material is 420 µm to 590 µm. A −40 to +60 mesh screening contains all particles passing a 40 mesh screen and retained on a 60 mesh screen. The particle size range for this material is 250 µm to 420 µm. A −60 to +80 mesh screening contains all particles passing a 60 mesh screen and retained on an 80 mesh screen. The particle size range for this material is 180 µm to 250 µm. A −60 mesh screening contains all gradations passing a 60 mesh screen. All this material is less than 250 µm in size. A −80 mesh screening collects the finest of the material and includes all gradations passing an 80 mesh screen. All material from this screen is less than 150 µm in size.

Advantageously, ball milling of aragonite produces an aragonite particle/powder having an improved (less varied) size distribution than conventional ground calcium carbonate (GCC). For example, with reference to FIG. 2, ball milled aragonite using the system and methods disclosed herein, can produce an aragonite particle of 2.5 to 3.5 micron size with a clean top size. A clean top size means that very few particles are larger than the 3.5 micron size when produced using this system and method with a classifier set at 2.5 to 3.5 micron size range. For example, for aragonite produced in this set range using the disclosed system, only <0.0005% are retained on a 325 mesh and only slightly more <0.0007% are retained on a 500 mesh, as compared to a GCC product having the same median (D50) particle size distribution (PSD). Accordingly, aragonite produced using the contemplated system and methods have a cleaner top size than conventional GCC.

With continued reference to FIG. 2, an exemplary method using a ball milling system in general includes: 1) characterized or characterizing aragonite (e.g., obtained from ocean reefs); 2) providing the aragonite to a feed hopper to set; 3) exposing the aragonite to an electromagnet to prevent and/or remove any metal contamination; 4) processing the aragonite in a fluid bed dryer; 5) screening the aragonite through a screen stack; 6) grinding the aragonite in a ball mill; 7) passing the aragonite exiting the ball mill through an air classifier to size the aragonite particles and direct the oversized particles back through the ball mill and direct particles of desired size to be processed through a heat jacketed mixer.

More specifically, the starting aragonite obtained from natural sources may be initially characterized using sieve analysis. In addition to various sized particles, the starting aragonite (as sourced) has approximately 2-3% by weight amino acids. Typically, the starting aragonite has a median (D50) micron size between 700-800 um (e.g., 750 um). Using the disclosed closed circuit ball milling system and method, the 700-800 um starting aragonite is processed to a 2.5 to 3.5 micron aragonite product with a cleaner top size compared to GCC.

Providing the starting aragonite to a feed hopper the feed rate of the aragonite material within the system can be controlled. Preferably a grizzly feed hopper is used having a grizzly section (i.e., grizzly bars) with openings that allow undersized material to pass before discharging into a crusher or grinder. Additionally, a grizzly feed hopper vibrates in order to force the material toward the discharge end while segregating the material.

In an exemplary embodiment, with reference to FIG. 2, from the feed hopper (2) the aragonite is moved out of the hopper at a flow rate suitable for the desired particle size. For example, for particles between 2.5 to 3.5 microns, a suitable flow rate is of between 6,500 to 7,000 pounds/hour (lbs/hr).

With continued reference to FIG. 2, if it is desired to prevent or in the least decrease metal contamination of the aragonite, the aragonite may be fed out of the feed hopper to an electromagnet (3). If the electromagnet is used, after exposure to the electromagnet, the aragonite is provided to a fluid bed dryer (4) to reduce the moisture content of the aragonite. Surprisingly, while the moisture content is decreased by drying at a temperature between 200-300° Fahrenheit (F), the contemplated method ensures the aragonite is processed at temperatures below 200° Celsius (C). It is noted that at temperatures above 200° C., the inherent 2-3% amino acid content in the aragonite degrades, rendering the aragonite more hydrophilic, thereby increasing the moisture content of the aragonite by 10,000 to 30,000 ppm. Without wishing to be bound by any theory, the temperatures for the steps of the contemplated method are less than 200° C. Typically, the temperature of the fluid drying bed is of between 200-300° F., and preferably, the temperature is 260° F.

The contemplated ball milling system feeds the aragonite from the fluid bed dryer (4) to a screen stack (5) (FIG. 2). In some embodiments, the screen stack includes a set of graded sieve meshes. For example, for an aragonite particle having a PSD of 2.5 to 3.5 microns, the set of stacked screens may include: 1) 1 inch; and 2) 4 mesh. In some embodiments, the stacked screens may include 1) 1 inch; 2) 4 mesh; and 3) 24 mesh. In still other embodiments, the stacked screens may include 1) 1 inch; 2) 4 mesh; 3) 24 mesh; and 4) 80 mesh.

From the output of the stacked screens, the screened aragonite is directed into a mill to be ground. The aragonite is fed into the mill at a rate equal to the production output of the milling circuit. The mill may be a vertical mill or a horizontal ball mill (6) as depicted in FIG. 2. Preferably the mill is a closed circuit ball milling system. As depicted, a closed circuit system includes a classifier that isolates products larger than the set size and returns the oversized product to the ball mill to be mixed with "new" aragonite material and reground. The aragonite material fed into the ball mill mixes with the classifier rejects and is ground inside the ball mill with metal grinding media. Exemplary metal grinding media include carbon steel, forged steel, stainless steel, or chrome steel grinding balls. More specifically, the size of the metal grinding balls is selected depending on the desired particle size. For example, for aragonite particles having a PSD of 2.5 to 3.5 microns, ⅜ inch metal grinding balls may be used. Preferably, the volume of grinding balls should be between 40-45% of the inside shell volume of the mill. With the addition of the aragonite material, the volume is preferably at about 50-60%

As understood in the art, for ball milling, the optimum speed is the speed at which the centrifugal force at the top of the mill is just balanced by the force of gravity, thereby causing the balls to be lifted to the maximum height before they fall onto the balls/material below and imparting the most kinetic energy. In practice, the ball mill is typically run just below the optimum speed—e.g., 70-80% of the optimum speed. More typically, the ball mill is run at 75% of the optimum speed—corresponding to approximately 30 rotations per minute (rpm).

The contemplated method using dry mill processing, may also include adding a grinding aid. In preferred embodiments, the grinding aid HEA-2/MTDA 632 is added. More preferably, the grinding aid is added at a rate of 12 to 15 cc/minute. Most preferably, the grinding aid is added at rate of 12 to 15 cc/minute and at 30 to 100 ppms.

With respect to the ball mill device or any type of dry mill device, the specific dimensions and overall size of the mill will depend on the volume of aragonite to be processed as well as the desired particle size. For example, the ball mill disclosed in FIG. 2 has a diameter of 4 feet (4') and a length of 12 feet (12'). Additionally, in preferred embodiments, the inside of the mill has a ceramic lining. Most preferably, the ball mill is a grate discharge ball mill which allows for a steep particle size distribution in a closed circuit mill having a classifier with the rejects being recycled. Preferably, with grate discharge design, the volume of the grinding media and the aragonite material is higher at the feed end of the mill (e.g., between 55-60%) and decreases to 50-55% at the discharge end of the mill. Accordingly, the grate discharge configuration allows for the grinding energy of the ball mill to be concentrated on the coarse particles, thereby lending to a "clean top" particle distribution.

Surprisingly, processing aragonite particles using a ball mill as disclosed herein, utilizes less energy (e.g., horsepower (hp); hp/ton) than the production of ground calcium carbonite (GCC) using conventional wet ground methods. For example, for making a 2 to 3 micron particle, the ball mill system as described herein and depicted in FIG. 2 uses 125-175 hp/ton.

As disclosed, the contemplated ball mill system recycles any oversized particles coming out of the ball mill grinder in order to keep the particle size distribution (PSD) close to the upper set size without much variation, resulting in a "clean top" PSD. The classifier receiving the aragonite from the ball mill may be any suitable classifier. For example, as depicted in FIG. 2, an air classifier (7) is used (e.g., MS-10 or MS-5 air classifier) with an original equipment manufacturer (OEM) micro sizer and a fines recovery of 12-20%. Preferably the air classifier separates the fine and coarse material by a rotating classifier and air flow. For example, for a 2.5 to 3.5 micron product, the classifier rotates at 1600 to 1800 rpms with a fan set at approximately 3,800 rpms.

For aragonite particles that are not surface treated, the aragonite that passes from the classifier having the set particle size is ready for packaging.

In some embodiments, the aragonite produced from the ball mill may be surface treated. Accordingly, after the aragonite passes through the classifier with the set particle size, it is then directed from the classifier (7) to a heat jacked mixer (8). Aragonite having 2-3% amino acid content has a hydrophilic surface. However, for example, if a hydrophobic surface is desired, the aragonite particle may be treated with steric acid. The heat jacked mixer provides the application of the steric acid (e.g., palm based steric acid at 1.6-1.9%) and a temperature of 270-290° F. The heated application of the steric acid ensures the particle has a monolayer of steric acid coating.

Alternatively, the application of steric acid to the aragonite may be applied in a pen mill with liquid steric acid.

As will be further appreciated, the comminuted aragonite materials may be further subjected to chemical and/or physical modifications, including coatings and/or heat setting. For example, coatings may impart color, desirable compounds such as amino acids, proteins, waxes etc., or add bacteria. Physical modifications include heat setting and/or ionizing to impart or remove a specific Zeta charge on the material, which will significantly impact various material properties of the modified aragonite.

The carrier disclosed in the instant composition comprises an aqueous solution. In some embodiments, the composition may comprise from about 40% to about 99%, preferably from about 50% to about 98%, and more preferably from about 80% to about 95% by weight of water, relative to the total weight of the composition.

Alginate Carrier

In some embodiments, aragonite is encapsulated in a carrier. In typical embodiments, the carrier may comprise a water-soluble alginate hydrogel. Alginate may also be referred to as alginic acid or alginate. Alginate is a biomaterial made from algae or seaweed. Structurally, alginate is an anionic polysaccharide formed by linear block copolymerization of d-mannuronic acid and 1-guluronic acid. As such, alginates are linear unbranched polysaccharides which contain different amounts of (1→4')-linked β-d-mannuronic acid and α-1-guluronic acid residues. Alginate has numerous applications in biomedical science and engineering because of its favorable properties, including biocompatibility and ease of gelation. Alginate is typically used in hydrogel form. Hydrogels are three-dimensionally cross-linked networks composed of hydrophilic polymers with high water content. Chemical and/or physical cross-linking of hydrophilic polymers are typical approaches to form hydrogels. Various approaches may be used to cross-link alginate chains to prepare gels, such as ionic cross-linking, covalent cross-linking, or thermal gelation. See Lee, Kuen Yong and David J Mooney. "*Alginate: properties and biomedical applications*" Progress in polymer science vol. 37, 1 (2012): 106-126.

The alginate hydrogel's physicochemical properties depend on the alginate's molecular weight, in addition to the cross-linking type and cross-linking density. Thus the skilled artisan can adjust the alginate's molecular weight, depending on the composition's intended use, to achieve desired gel solution viscosity and post-gelling stiffness. In one embodiment, the molecular weight ranges between 32,000 and 400,000 g/mol. In one embodiment, the compositions disclosed herein comprise oolitic aragonite beads and a water soluble alginate hydrogel—a completely ocean derived personal care product or cosmetic product.

Applications and Uses

The aragonite particles processed according to the methods disclosed herein-using for example, the contemplated ball mill system—may be utilized in a vast array of applications including cleansers and cosmetics, drug delivery nanoparticles, and chromatography media, as more specifically described herein.

Chromatography (e.g., ion exchange chromatography) requires relatively costly chromatography media (e.g., adsorptive beads) for the separation and purification of biological samples (e.g., proteins, antibodies). Accordingly, aragonite from abundant biogenic sources including mollusk shells and corals may be processed using the ball mill system and methods as disclosed herein and used as chromatography adsorbent media. In particular, the aragonite particles may be used as hydrophilic or hydrophobic chromatography media for use in gravity isolation methods as well as column chromatography. As described herein, aragonite inherently has a hydrophilic surface and may be surface treated to render a hydrophobic surface. Furthermore, aragonite particles having either a hydrophilic or hydrophobic surface may be further functionalized with corresponding binding molecules or binding moiety for more specific binding of target molecules.

In other contemplated applications, the aragonite particles made by the methods and systems disclosed herein, may be used as carriers for therapeutic drugs. For example, chemotherapeutics (e.g., small molecules) may be loaded onto aragonite particles, wherein release of the small molecules is pH dependent. See, e.g., Kamba et al. (2013) *J. Nanomaterials* 2013:398357 and Kamba et al. (2013) *Biomed Res. Intl.* 2013:587451. Accordingly, the aragonite particles produced by the presently disclosed method and system including the application of a surface treatment, provide an aragonite particle capable of effectively delivering a drug therapy, including targeted cancer therapy.

In some aspects of the invention, the presently disclosed aragonite particles may be processed as disclosed herein and surface treated (e.g., with steric acid) in order to produce an effective nanoparticle for loading small molecule chemotherapeutics. In addition, surface treated aragonite particles as disclosed herein may be further functionalized for loading of larger molecule biologics, including proteins and antibodies.

Oolitic aragonite naturally has an alkaline pH (around 8.2 to 8.4), which makes it an effective cleanser to clean the acid mantle on the surface of the skin. Because the acid mantle is acidic, the most effective ways to clean the skin, along with excess oils, dirt and germs, all use alkaline compositions.

In one embodiment, the oolitic aragonite composition disclosed herein may be useful in a cleansing composition, such as a bath or shower gel, a face cleanser, shampoo, soap bar, toothpaste, or a dishwashing liquid. In these embodiments, the composition further comprises a surfactant, and preferably a cosmetically acceptable surfactant. The surfactant may be chosen from anionic surfactants, nonionic surfactants, amphoteric surfactants, zwitterionic surfactants, and mixtures thereof. Such a cleansing composition is a rinse off product, such that the composition is applied and then rinsed off.

Anionic surfactants as disclosed herein include surfactants comprising anionic groups. These anionic groups are preferably chosen from —$CO_2H$, —$CO_2^-$, —$SO_3H$, —$SO_3^-$, —$OSO_3H$, —$OSO_3^-$, —$H_2PO_3$, —$HPO_3^-$, —$PO_3^{2-}$, —$H_2PO_2$, =$HPO_2$, —$HPO_2^-$, =$PO_2^-$, =POH, and =$PO^-$ groups. The anionic surfactant may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglycoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids, and the corresponding non-saltified forms of all these compounds, the alkyl and acyl groups of all these compounds comprising from 6 to 24 carbon atoms and the aryl group denoting a phenyl group. Another group of anionic surfactants that may be used is that of acyl lactylates, the acyl group of which comprises from 8 to 20 carbon atoms. The anionic surfactant may also be made of alkyl-D-galactoside-uronic acids and their salts, and also of polyoxyalkylenated ($C_{6-24}$) alkyl ether carboxylic acids, polyoxyalkylenated ($C_{6-24}$) alkyl ($C_{6-24}$) aryl ether carboxylic acids, polyoxyalkylenated ($C_{6-24}$) alkylamido ether carboxylic acids and salts thereof, especially those containing from 2 to 50 ethylene oxide units, and mixtures thereof. When the anionic surfactant(s) are in salt form, they may be chosen from alkali metal salts such as the sodium or potassium salt, ammonium salts, amine salts, and in particular amino alcohol salts or alkaline-earth metal salts such as the magnesium salts. Examples of amino alcohol salts that may especially be mentioned include monoethanolamine, diethanolamine, and triethanolamine salts, monoisopropanolamine, diisopropanolamine, or triisopropanolamine salts, 2-amino-2-methyl-1-propanol salts, 2-amino-2-methyl-1, 3-propanediol salts, and tris (hydroxymethyl) aminomethane salts. Alkali metal or alkaline-earth metal salts, and in particular sodium or magnesium salts, are preferably used.

Nonionic surfactants as disclosed herein include surfactants such as oxyalkylenated (more particularly polyoxyethylenated) esters of fatty acids and of glycerol, oxyalkylenated esters of fatty acids and of sorbitan, oxyalkylenated (oxyethylenated and/or oxypropylenated)

esters of fatty acids (e.g., ARLACEL 165), oxyalkylenated (oxyethylenated and/or oxypropylenated) ethers of fatty alcohols, esters of sugars, such as sucrose stearate, ethanolamine and its derivatives, such as cocamide MEA, or ethers of fatty alcohol and of sugar, in particular alkyl polyglucosides (APGs), such as decyl glucoside and lauryl glucoside, cetostearyl glucoside, optionally as a mixture with cetostearyl alcohol, and arachidyl glucoside, for example in the form of the mixture of arachidyl alcohol, behenyl alcohol and arachidyl glucoside.

Amphoteric or zwitterionic surfactants as disclosed herein include derivatives of optionally quaternized aliphatic secondary or tertiary amines, where the aliphatic group is a linear or branched chain comprising from 8 to 22 carbon atoms, the amine derivatives contain at least one anionic group, for instance a carboxylate, sulfonate, sulfate, phosphate or phosphonate group. Examples of amphoteric or zwitterionic surfactants include $(C_{8-20})$ alkylbetaines, sulfobetaines, $(C_{8-20})$ alkylamido $(C_{3-8})$ alkylbetaines and $(C_{8-20})$ alkylamido $(C_{6-8})$ alkylsulfobetaines. It should also be appreciated the aragonite materials according to the inventive subject matter can be modified to change or remove the zeta potential of the aragonite, which will significantly affect the physicochemical properties of the aragonite (e.g., enhance or reduce binding of cationic or anionic materials, enhance or reduce particle repulsion, etc.).

The compositions disclosed herein may further comprise a protein in an amount about 0.001% (w/w) to about 1% (w/w) of the total weight of the composition. A variety of proteins may be used that offer a beneficial effect or nourishment to hair or skin. For example, milk protein casein may be used for its moisturizing effect. Collagen and elastin may be used in the composition disclosed herein to improve the skin's elasticity and to reduce or eliminate wrinkles. Keratin may be used in the composition, especially if it is used in the hair, to improve hair quality and texture. Albumin may be used in the composition to soothe the skin and promote healing, and to enhance wound healing.

Antioxidants and vitamins may also be added to the composition to provide additional benefits to the skin or hair. Furthermore, the composition may also comprise solvents, emulsifiers, surfactants, structuring agents, thickeners or gelling agents, skin conditioning agents, fillers, fibers, sunscreen agents, preservatives, perfumes (e.g., fragrant essential oils and/or aroma compounds), chelators, antioxidants, neutralizing or pH-adjusting agents, cosmetically active agents, dermatologically active agents, flavonoids, colorants, aesthetic agents, foam enhancers, botanical extracts, anti-inflammatory agents, and mixtures thereof.

Also disclosed herein are methods for reducing plastic contamination and/or pollution comprising making an exfoliating composition for a cosmetic or personal care product, wherein at least a portion of the plastic microbeads in the cosmetic or personal care product are replaced with oolitic aragonite. Plastic pollution is one of the greatest threats to ocean health worldwide, with between 4 and 12 million metric tons of plastic enter the ocean each year-enough to cover every foot of coastline on the planet. In the ocean, plastic pollution impacts sea turtles, whales, seabirds, fish, coral reefs, and countless other marine species and habitats. It is estimated that more than half of the world's sea turtles and nearly every seabird on Earth have eaten plastic in their lifetimes. The present disclosures solve this problem by replacing microbeads with oolitic aragonite in face scrubs, toothpastes, cosmetics, and bodywashes.

Oolitic aragonite in cosmetics for the skin, lips, eyebrows and eyelashes can achieve a homogeneous deposit of the cosmetic on these skin and hair surfaces, while at the same time providing softness. Make-up or cosmetic products, such as foundations, lipsticks, mascara, etc., generally contain (a) an aqueous base and/or a fatty phase such as waxes and oils, (b) pigments to bring color to the cosmetic, (c) fillers and (d) optional additives such as cosmetic or dermatological active agents. The fillers generally serve to modify the texture of the composition and in particular to rigidify it as well as to give a matte effect to the film of composition deposited on the skin and/or the lips, which is particularly desired for users with combination or greasy skin, as well as for users in hot and humid climates.

Cosmetic fillers frequently comprise microbeads. As explained herein, oolitic aragonite may be used to replace some, if not all, of the microbeads in cosmetics, without any negative consequences to the texture, look, or feel of the cosmetic. Thus, in one embodiment, at least 30% (w/w), for example at least 40%, at least 50%, at least 60%, at least 70%, at least 80%, at least 90%, at least 95%, at least 96%, at least 97%, at least 98%, at least 99%, or even 100% (w/w) of the plastic microbeads in cosmetics may be replaced with oolitic aragonite particles. Oolitic aragonite is preferably present in the cosmetic composition in a content of from about 0.1% (w/w) to 70% (w/w), more preferably about 4% to 70%, and most preferably from about 4% to 50%. Because the plastic microbeads are replaced with oolitic aragonite, there is correspondingly less plastic in the compositions described herein. Therefore, in certain embodiments plastic microbeads comprise no more than 50% (w/w) of the compositions disclosed herein, for example no more than about 45%, no more than about 40%, no more than about 35%, no more than about 30%, no more than about 25%, no more than about 20%, no more than about 15%, no more than about 10%, no more than about 5%, no more than about 4%, no more than about 3%, no more than about 2%, no more than about 1%, no more than about 0.5%, no more than about 0.1%, or no more than about 0.01% (w/w) of plastic.

When used in cosmetic products, the oolitic aragonite particles have a diameter ranging from about 1 nm to 500 µm, more preferably from 1 µm to 200 µm, and most preferably from about 10 µm to 100 µm. Alternatively, at least 30%, at least 50%, at least 70%, at least 90% of the oolitic aragonite particles have an average diameter between about 1 nm to 500 µm, or more preferably from 1 µm to 200 µm, and most preferably from about 10 µm to 100 µm. These particles can be spherical, platelet shaped, oval shaped, flat, or amorphous. Spherical shapes are preferred.

Oolitic aragonite disclosed herein may also be used as nacres, or iridescent particles, to modify cosmetic texture, as well as matte/gloss effect. When 1 nm to 100 µm oolitic aragonite particles are used as iridescent particles, the particles may be coated. For example, oolitic aragonite coated with titanium or with bismuth oxychloride achieves a white pearlescence, while oolitic aragonite coated with iron oxides, ferric blue, chromium oxide, bismuth oxychloride, or combinations thereof can achieve a colored pearlescence. Besides the oolitic aragonite, iridescent cosmetic compositions may also comprise an aqueous phase, a fatty phase (e.g., waxes/oils), a pigment to bring color to the cosmetic, a filler, and optionally an additive such as a cosmetically active agent or a dermatologically active agent, as described previously. In addition, it should further be appreciated that the size of (milled) aragonite will also have a substantial effect on brightness of the material. For example, when milled to a fine particle size of 2 to 8 micron, the Hunter brightness level is approximately 94, which is very bright white. Thus, by selecting a suitable particle size, brightness of the milled aragonite can be adjusted.

Oolitic aragonite compositions as described herein may also be used in toothpaste, along with other dental agents and fillers, where the oolitic aragonite serves as an abrasive. Advantageously, aragonite's calcium carbonate may also be helpful for remineralization. Toothpastes as described herein may optionally incorporate fluoride as an anti-cavity agent. Oolitic aragonite preferably comprises about 0.1% to 40% (w/w), more preferably about 0.4% to 35%, and most preferably from about 4% to 15%. Oolitic aragonite may have any suitable shape dictated by manufacturing, as well as other considerations. For example, while naturally occurring in the shape of crystalline needles, oolitic aragonite may be manufactured into various other geometries. The crosswise length of the oolitic aragonite should be sufficient-when measured at its widest point—to provide an abrasive quality, such as from 1 μm to 10 mm, or more preferably from 10 μm to 5 mm, and most preferably from 100 μm to 3 mm across. Besides oolitic aragonite, the toothpaste may also comprise other dental agents, such as for reducing cavities, reducing bacterial infection, preventing plaque build-up, reducing hypersensitivity, reducing gum inflammation, providing fluoride, reducing oral malodor, etc. The toothpaste is also contemplated to comprise a carrier, such as sorbitol.

Additional embodiments of the contemplated subject matter include making a synthetic pearl composition. Natural pearls and cultured pearls are made of aragonite or a mixture of aragonite and calcite in minute crystalline form. The natural or cultured pearl is formed from deposition of layers of aragonite. As used herein, "synthetic" refers to a pearl composition that is manufactured. The presently disclosed synthetic pearl composition is not necessarily molecularly different from a natural or cultured pearl. The layering of aragonite occurs most commonly in an oyster to form natural and cultured pearls, whereas a synthetic pearl composition is made by machine-compressed aragonite.

For the manufacturing of a synthetic pearl composition, the contemplated method includes providing aragonite microbeads having an average particle size of between 100 nm to 1 mm, as disclosed herein to a device capable of withstanding and/or applying pressure. In typical embodiments, the aragonite microbeads have an average particle size of between 1 nm to 200 μm. The applied pressure to form a synthetic pearl composition made of compressed layered aragonite may be from about 4,000 up to about 10,000 pounds per square inch (psi). Typically, the applied pressure is of between about 5,000 to 7,000 psi.

The synthesized pearl composition may be formed in any shape. For example, the aragonite microbeads may be provided into a mold of any shape prior to the application of pressure. For example, synthetic pearl compositions may take the form of sheets or spheres. The application of pressure may be from one or multiple directions. The direction of the pressure may be determined by the desired shape of the synthetic pearl composition. In contemplated examples, the applied pressure to the aragonite particles may be from one direction, two opposing directions, or from more than 2 directions. The pressure may be a balanced pressure in which each applied pressure or force applied to the aragonite particle composition is balanced by an opposing pressure or force from the opposite direction with respect to the aragonite microbeads. The resulting pearl composition may vary depending on the amount and/or direction of pressure applied to the aragonite particles.

A pressure device for compressing the aragonite microbeads to produce the synthetic pearl composition may be of one of many suitable machines. For example, the pressure device may be a roller device similar to a pasta roller or polymer clay roller in which the aragonite microbeads are provided between two opposing rollers configured to apply pressure to the material therebetween to thereby produce a pressed sheet composition. In typical embodiments, the roller device is capable of applying a pressure of between 5,000 to 7,000 psi. Whereas a roller device produces a sheet composition between the rollers, other suitable pressure devices may include a mold for holding the aragonite microbeads wherein the mold is capable of withstanding the applied pressure to form a synthetic pearl composition in the shape of the mold.

It should be apparent to those skilled in the art that many more modifications besides those already described are possible without departing from the concepts described herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Where the specification claims refers to at least one of something selected from the group consisting of A, B, C . . . and N, the text should be interpreted as requiring only one element from the group, not A plus N, or B plus N, etc.

What is claimed is:

1. A composition comprising oolitic aragonite particles, wherein the oolitic aragonite particles have an average particle size of between 100 nm to 1 mm, and a median (D50) particle size distribution (PSD) of between 2.0 to 3.5 μm, and a Hunter brightness level of about 94.

2. The composition of claim 1, wherein the oolitic aragonite particles have a D50 PSD of between 2.5 to 3.5 μm.

3. The composition of claim 1, wherein the oolitic aragonite particles are loaded with a molecule.

4. The composition of claim 1, wherein the oolitic aragonite particles are surface treated.

5. The composition of claim 3, wherein the molecule is a chemotherapeutic.

6. The composition of claim 3, wherein the molecule is a protein and the oolitic aragonite particles are functionalized to bind the protein.

7. The composition of claim 1, wherein the oolitic aragonite particles are formulated as chromatography media.

8. The composition of claim 1, wherein the oolitic aragonite particles are formulated as a synthesized pearl composition.

9. The composition of claim 1, wherein the oolitic aragonite particles are milled.

10. The composition of claim 1, wherein the oolitic aragonite particles are ball milled.

* * * * *